United States Patent [19]

Buendia et al.

[11] Patent Number: 5,384,419
[45] Date of Patent: Jan. 24, 1995

[54] PREPARATION PROCESS FOR 20-KETO-21(S) HYDROXY STEROID COMPOUNDS AND INTERMEDIATES

[75] Inventors: Jean Buendia, Le Perreux Sur Marne; Jean-Yves Godard, Le Raincy; Philippe Mackiewicz, Livry Gargan; Christian Richard, Rosny Sous Bois, all of France

[73] Assignee: Roussel-Uclaf, France

[21] Appl. No.: 71,199

[22] Filed: Jun. 2, 1993

[30] Foreign Application Priority Data

Jul. 23, 1992 [FR] France .................. 92 09077

[51] Int. Cl.⁶ ........................... C07J 5/00
[52] U.S. Cl. ........................ 552/556; 552/552; 552/544; 435/52; 435/54; 435/58
[58] Field of Search ............ 552/555, 556; 435/52, 435/54, 58

[56] References Cited

FOREIGN PATENT DOCUMENTS 0007823  6/1980  France .

OTHER PUBLICATIONS

Nuclear Medecine and Biology by Martin G. Pomper, et al. vol. 17, No. 3, 1990 Oxford GB pp. 309–319.

*Primary Examiner*—Johann Richter
*Assistant Examiner*—Rebecca Cook
*Attorney, Agent, or Firm*—Bierman and Muserlian

[57] ABSTRACT

An improved process for the preparation of 20-keto-21(S)-hydroxy steroids of the Formula

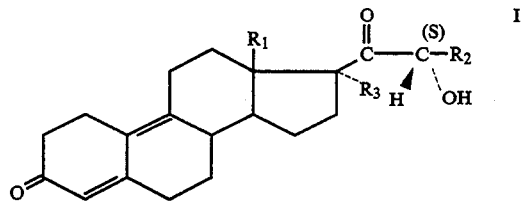

wherein $R_1$ is alkyl of 1 to 3 carbon atoms, $R_2$ is alkyl of 1 to 12 carbon atoms, and $R_3$ is alkyl of 1 to 4 carbon atoms and novel intermediates therefrom.

10 Claims, No Drawings

PREPARATION PROCESS FOR 20-KETO-21(S) HYDROXY STEROID COMPOUNDS AND INTERMEDIATES

OBJECTS OF THE INVENTION

It is the object of the invention to provide an improved process for the preparation of 20-keto-21(S)-hydroxy steroids and novel intermediates therefrom.

This and other objects and advantages of the invention will become obvious from the following detailed description.

THE INVENTION

The novel process of the invention for the preparation of a compound of the formula

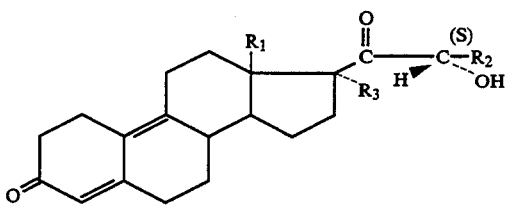

wherein $R_1$ is alkyl of 1 to 3 carbon atoms, $R_2$ is alkyl of 1 to 12 carbon atoms and $R_3$ is alkyl of 1 to 4 carbon atoms comprises reacting a compound of the Formula

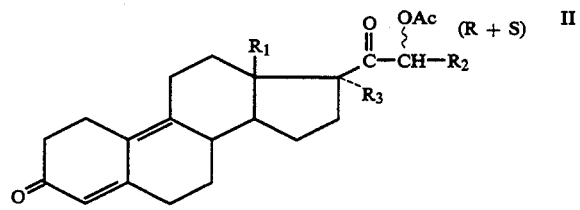

wherein $R_1$, $R_2$ and $R_3$ are as defined above in the form of a mixture of isomers on the 21-position, with a diastereo selective hydrolysis agent to obtain a mixture of the compounds of the Formulas

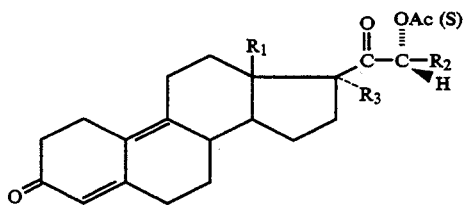

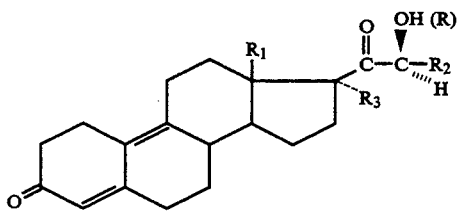

reacting the mixture with a compound of the Formula

Hal-SO$_2$-R      A wherein Hal is halogen and R is selected from the group consisting of alkyl of 1 to 6 carbon atoms, —CX$_3$, and phenyl optionally substituted with at least one alkyl of 1 to 3 carbon atoms, and X is fluorine, chlorine, or bromine, to obtain a mixture of a compound of Formula II$_1$ and a compound of the Formula

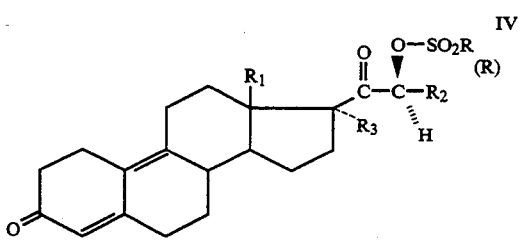

and either reacting the mixture with an alkali metal acetate to obtain the compound of Formula II$_1$, and subjecting the compound of Formula II$_1$ to solvolysis in a basic medium or reacting the mixture of the compound of Formula II$_1$, and the compound of Formula IV with a basic and nucleophilic hydroxylating agent to obtain the compound of Formula I.

Examples of $R_1$ are methyl, ethyl, and propyl, with methyl being preferred; examples of $I_3$ are methyl, ethyl, and n-propyl. Examples of $R_2$ are methyl, ethyl, propyl, isopropyl, n-butyl, isobutyl, n-pentyl, n-hexyl, 2-methyl-pentyl, 2,3-dimethyl-butyl, n-octyl, and 2,2-dimethyl-hexyl.

The diastereoselective hydrolysis agent of the mixture of esters of Formula II can be enzyme such as esterase, or lipase; for example one of those known under the names of pancreatic porcine lipase, PS "Amano" (*Pseudomonas fluorescens*), A$_1$ "Enzymatix" (animal pancreatic lipase), Liposyme 10000 L (*a Mucor*), N "Amano" (*Rhizopus*), F$_8$"Enzymatix"(lipase), F$_3$ "Enzymatix"(*Mucor jevanicus*), B$_1$ "Enzymatix" (*Pseudomonas sp*) or *Pseudomonas fluorescens* lipase. The lipase known under the name PS "Amano" is preferred. The operation takes place at neutral pH or, preferably, weakly acidic pH, on the order of 5, obtained by the use of an appropriate aqueous buffer and, if appropriate, the addition of a base. The reaction takes place at ambient temperature or, preferably, slightly higher, on the order of 40° C. It can go forward in the presence of a cosolvent which can be an alkane such as hexane or, preferably, a lower alkanol such as n-butanol, propanol, or isopropanol.

The reagent of Formula A is preferably methane sulfonyl chloride, methane sulfonyl bromide, ethane sulfonyl chloride, ethane sulfonyl bromide, phenylsulfonyl chloride, phenylsulfonyl bromide, p-toluenesulfonyl chloride, p-toluenesulfonyl-bromide, trifluoromethylsulfonyl chloride, trifluoromethylsulfonyl bromide. The reagent is reacted in the presence of a basic agent which is preferably an amine, such as triethylamine, pyridine, or dimethylamino-pyridine, or a mineral base, such as an alkali metal hydroxide or carbonate in an organic solvent. The solvent is, for example, a halogenated solvent such as methylene chloride, chloroform, or dichloroethane or an aromatic or saturated hydrocarbon, such as benzene, toluene, or cyclohexane.

The inversion of the sulfonate of Formula IV in a mixture with the compound of Formula II$_1$ can be carried out with an SN$_2$-type nucleophilic substitution, by using an alkali metal acetate, especially sodium acetate or potassium acetate. The operation is carried out by heating in an aprotic polar organic solvent such as bis(2-methoxy ethyl) ether, dimethylformamide, dimethylacetamide, dimethylsulfoxide, or dimethylpyrrolidone.

The solvolysis is preferably an alcoholysis carried out in the presence of sodium hydroxide or potassium hydroxide. The alcohol used is a lower alkanol, preferably methanol or ethanol. The solvolysis can also be a hydrolysis using for example the bases mentioned above.

The inversion of the sulfonate can also be carried out by the action of a basic and nucleophilic hydroxylating agent which can be alkali metal hydroxide or alkaline-earth metal hydroxide, e.g. sodium hydroxide, potassium hydroxide, calcium hydroxide, or barium hydroxide. The operation is carried out in a solvent such as mixtures of tetrahydrofuran, bis(2-methoxyethyl) ether, triethyleneglycol dimethyl ether, dimethylformamide, dimethylsulfoxide, dimethylacetamide with water.

A quite particular subject of the invention is the process wherein the compound of Formula II has $R_1$, $R_2$ and $R_3$ all being methyl. Finally, the invention includes, as new industrial compounds, the mixture of the compounds of Formulas $II_1$ and III and the mixture of the compounds of Formulas $II_1$ and IV as defined previously.

The compounds of Formula I are endowed with progestomimetic and anti-estrogen activity, and are described in European Patent No. 7823. The starting compounds of Formula II are described in this same Patent.

The different enzymes mentioned above are commercially available product from, for example, the following companies: Amano Pharmaceutical Co. Ltd, Enzymatix Ltd, Sigma Chemie SARL, and Novo Nordisk Bio Industrie.

In the following examples, there are described several preferred embodiments to illustrate the invention. However, it should be understood that the invention is not intended to be limited to the specific embodiments.

EXAMPLE 1

17α-methyl-17β-(2S-hydroxy-1-oxo-propyl)-Δ4,9-estradien-3-one

Step A: Mixture of 17α-methyl-17β-(2R-hydroxy-1-oxo-propyl)Δ4,9-estradien-3-one and 17α-methyl-17β-(2S-acetoxy-1-oxo-propyl)-Δ-estradien-3-one.

5 g of 17α-methyl-17β-(2R, S-acetoxy-1-oxo-propyl)-Δ4,9-estradien-3-one, 5 g of PS "Amano" lipsase, 7 ml of n-butanol, and 18 ml of pH=5 buffer were mixed together and the temperature was maintained at 37° C. while the pH was kept at 5 by the addition of 1N sodium hydroxide. After 144 hours, 3.75 ml of pH=5 buffer, 1.25 g of PS "Amano" lipase were added and, after 168 hours, extraction took place with methylene chloride. The organic phase was washed with water, dried, and the solvent was evaporated to obtain 4.63 of the expected mixture containing approximately 50% of each of the constituents.

NMR Spectrum CDCl$_3$ (300 MHz)
—50/50 mixture of 2 constituents
1) 0.81 (s): 18—CH$_3$; 1.16 (s): 17—CH$_3$; 1.33 (d) CH$_3$—CH 3.71 (d): OH—; 4.56 (quintuplet): —C M—OH; 5.68 (s): H$_4$
2) 0.82 (s): 18—CH$_3$; 1.21 (s): 17—CH$_3$; 1.38 (d): CM$_3$—CH—; 2.11 (s) : O—Ac; 5.42 (q): CH$_3$— CH—; 5.68 (s): H$_4$.

The respective proportions of the two constituents of the mixture were also determined by HPLC comparatively with the pure constituents described and characterized in European Patent No. 7823 (Example 2).

Step A: Mixture of 17α-methyl-17β-(2R-hydroxy-1-oxo-propyl)-Δ4,9-estradien-3-one and 17α-methyl-17β-(2S-acetoxy-1-oxo-propyl)-Δ4,9-estradien-3-one.

0.1 g of 17α-methyl-17β-(2R,S-acetoxy-1-oxo-propyl)-Δ4,9-estradien-3-one, 2 ml of phosphate PH 7 buffer, and 20 mg of the enzyme shown in the table below were mixed together; the mixture was stirred (300/revs/min) while the pH was adjusted to maintain it between 5 and 8. The expected mixture was obtained after stirring 64 to 137 hours with (R) ester being hydrolyzed in the proportions shown in the table.

The reaction was followed by thin layer chromatography eluting with a toluene—ethyl acetate mixture (1-1). The composition of the final mixture was determined by HPLC on a PARTISIL No. 2102 D column, eluting with a hexane-methylene chloride-dioxane mixture (8-1-1). The following results were obtained:

| Enzyme used | % of R and S alcohols in the medium |
|---|---|
| PS Amano lipase | >99.5% of (R) |
| A$_1$ enzymatix lipase | 85%(R)–15%(S) |
| 10 000 L liposyme | 90%(R)–10%(S) |
| B$_1$ enzymatix lipase | >95% of (R) |
| Pseudomonas fluorescens | >90% of (R) |

Step B: Mixture of 17α-methyl-17β-(2R-methyl-sulfonyloxy-1-oxopropyl)-Δ4,9-estradien-3-one and 17α-methyl-17β-(2S-acetoxy-1-oxopropyl)-Δ4,9-estradien-3-one.

2 g of the product of Step A and 10 ml of methylene chloride were mixed together under an inert gas atmosphere and then 0.8 ml of triethylamine were added to the solution. The mixture was cooled to 0° C./−2° C. and then 0.35 ml of methane sulfonyl chloride were slowly added while maintaining the temperature of 0° C. to 2° C. The mixture was stirred for 1 hour and was then poured into 5 ml of water. Extraction was carried out with methylene chloride and the organic phase was washed with water, dried, and the solvent was evaporated to obtain 2.35 g of the expected mixture composed of approximately 46% of the (S) acetate and 54% of the (R) mesylate. (Determination by HPLC on PARTISIL column using hexane—methylene chloride—dioxane 80/10/10).

NMR Spectrum CDCl$_3$ (300 MHz)
50/50 mixture of the 2 constituents
1) 0.90 (s): 18—CH$_3$; 1.56 (d): CH$_3$—CH—; 3.16 (s): O—SO$_2$—CH$_3$.
2) 0.82 (s): 18—CH$_3$; 1.39 (d): 17—CH$_3$—CH—; 2.11 (s): OAc; and, in addition, 1.18 (s) and 1.20 (s): 17—CH$_3$; 5.42 (q) and 5.52 (q): —OC—CH—CH$_3$; 5.68 (s): H$_4$ Step c: 17α-methyl-17β-(2S-acetoxy-1-oxopropyl)-Δ4,9-estradien-3 -one 1 g of the product of Step B and 7 ml of bis (2-methoxy ethyl) either were mixed together under an inert gas atmosphere and 0.38 g of potassium acetate were added to the solution followed by heating to 90 ° C. for 22 hours. After cooling to ambient temperature, the mixture was poured into 20 ml of water, and stirred for 4 hours. The product was separated, rinsed with water and then dried to obtain 0.77 g of the expected product containing approximately 94% of isomer (S). (Determination by HPLC as in Step B. )

NMR Spectrum CDCl$_3$ (300 MHz)

Presence of approximately 95% of the constituent characterized as follows:

0.82 (s) : 18—CH$_3$; 1.20 (s) ·17—CH$_3$; 1.39 (d) and 5.42 (q): CH$_3$—CH—; 2.11 (s): O—Ac; 5.69 (s) : H$_4$.

Step D: 17α-methyl-17β-(2S-hydroxy-1-oxopropyl)-Δ4,9-estradiene-3-one 0.5 g of the product of Step C, 4 ml of methanol and 0.5 ml of methanolic potassium hydroxide at 0.06 g/5 ml were mixed together and the solution was stirred for 4 hours at 20° C., then neutralized by the addition of 0.7 ml of 0.1 N hydrochloric acid. 5 ml of methylene chloride and 3 ml of water were added, followed by decanting and reextracting the aqueous phase with methylene chloride. The combined organic phases were dried and the solvent was evaporated to obtain 0.427 g of the expected product containing 94% of (S) isomer.

(Determination by HPLC as in Steps B and C).

NMR Spectrum CDCl$_3$ (300 MHz)

Presence of approximately 95% of 21(S) compound as characterized in Example 1 of European Patent No. 7823 (isomer A).

EXAMPLE 2

17α-methyl-17β-(2S-hydroxy-1-oxo-propyl)-Δ4,9-estradien-3-one 100 mg of the product of Step B of Example 1, 3 ml of solvent, and 100 mg of base were mixed together under an inert gas atmosphere. The mixture was heated with stirring and the reaction was monitored by HPLC. (Partisil column—eluant: hexane—methylene chloride—dioxane 8/1/1) The precise conditions and the results are shown in the table below.

| Base | Solvent | Temperature | Duration of reaction | % of expected products in the crude product |
|---|---|---|---|---|
| Ca(OH)$_2$ | Diglyme* + water | 90° C. | 1 H | 80% |
| NaOH | Dimethyl acetamide + water | 80° C. | 10 H | 73% |
| Ba(OH)$_2$ | Tetrahydrofuran + water | 80° C. | 24 H | 67% |

*bis(2-methoxyethyl) ether

Various modifications of the process of the invention may be made without departing from the spirit or scope thereof and it is to be understood that the invention is intended to be limited only as defined in the appended claims.

What we claim is:

1. A process for the preparation of a compound of the Formula

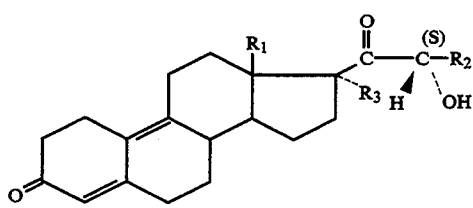

wherein R$_1$ is alkyl of 1 to 3 carbon atoms, R$_2$ is alkyl of 1 to 12 carbon atoms, and R$_3$ is alkyl of 1 to 4 carbon atoms, said process comprising reacting a compound of the Formula

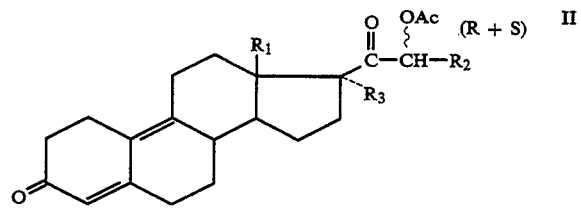

wherein R$_1$, R$_2$ and R$_3$ are as defined above in the form of a mixture of isomers on the 21-position with a diastereo selective hydrolysis agent to obtain a mixture of compounds of the Formulae

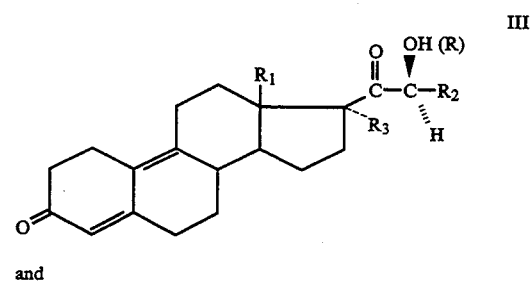

and

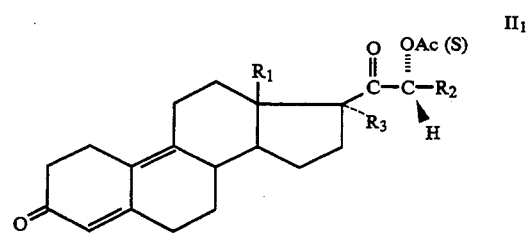

reacting the mixture with a compound of the Formula

Hal-SO$_2$-R     A wherein Hal is halogen and R is selected from the group consisting of alkyl of 1 to 6 carbon atoms, —CX$_3$, and phenyl optionally substituted with at least one alkyl of 1 to 3 carbon atoms, and X is fluorine, chlorine, or bromine, to obtain a mixture of a compound of Formula II$_1$ and a compound of the Formula

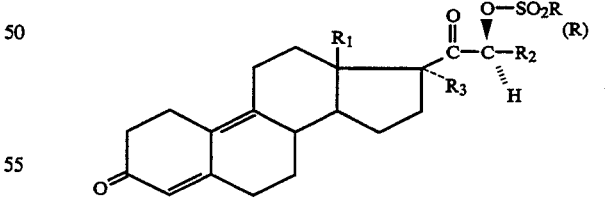

and either reacting the mixture with an alkali metal acetate to obtain the compound of Formula II$_1$, and subjecting the compound of Formula II$_1$ to solvolysis in a basic medium or reacting the mixture of the compound of Formula II$_1$ and the compound of Formula IV with a basic and nucleophilic hydroxylating agent to obtain the compound of Formula I.

2. The process of claim 1 wherein the diastereoselective hydrolysis agent is an enzyme.

3. The process of claim 2, wherein the enzyme is selected from the group consisting of porcine pancreatic lipase, *Pseudomonas fluorescens* lipase, animal pancreatic lipase, a mucor, rhizopus, *mucor javanicus, pseudomonas sp* lipase and *Pseudomonas fluorescens* lipase.

4. The process of claim 1 wherein the diastereoselective hydrolysis agent is *Pseudomonas fluorescens* lipase.

5. The process of claim 1 wherein the hydrolysis takes place at a neutral or weakly acidic pH.

6. The process of claim 1 wherein Formula A is selected from the group consisting of methanesulfonyl chloride, methane sulfonyl bromide, ethane sulfonyl chloride, ethane sulfonyl bromide, p-toluene sulfonyl chloride, p-toluene sulfonyl bromide, phenylsulfonyl chloride, phenylsulfonyl bromide, trifluoromethylsulfonyl chloride and trifluoromethylsulfonyl bromide.

7. The process of claim 1 wherein the alkali metal acetate is sodium or potassium acetate.

8. The process of claim 1 wherein the solvolysis is carried out with sodium hydroxide or potassium hydroxide in a lower alkanol.

9. The process of claim 1 wherein the basic and nucleophilic hydroxylating agent is selected from the group consisting of sodium hydroxide, potassium hydroxide, calcium hydroxide and barium hydroxide.

10. The process of claim 1 wherein in the compound of Formula II $R_1$, $R_2$ and $R_3$ are methyl.

* * * * *